United States Patent [19]
Austin, Jr. et al.

[11] Patent Number: 5,398,899
[45] Date of Patent: Mar. 21, 1995

[54] ROTATION ADJUSTMENT FOR DENTAL INSTRUMENT HOLDER

[75] Inventors: George K. Austin, Jr.; Pierre M. LaPlante, both of Newberg, Oreg.

[73] Assignee: A-Dec, Inc., Newberg, Oreg.

[21] Appl. No.: 12,737

[22] Filed: Feb. 3, 1993

[51] Int. Cl.⁶ .................................................. F16M 13/00
[52] U.S. Cl. .................... 248/222.1; 403/404; 403/362; 211/69; 248/291
[58] Field of Search ............... 248/291, 185, 222.1, 248/224.3; 211/69, 70.6; 403/379, 404, 362, 297, 162, 165

[56] References Cited

U.S. PATENT DOCUMENTS

| | | | |
|---|---|---|---|
| D. 211,689 | 7/1968 | Olsen | D24/1 |
| D. 243,188 | 1/1977 | Meyer | D24/1 B |
| D. 328,791 | 8/1992 | Nordstrom et al. | D24/177 |
| 1,276,463 | 8/1918 | Wells | 403/362 X |
| 1,891,048 | 12/1932 | Keefe | 248/222.1 |
| 1,893,729 | 1/1933 | Call | 248/222.1 |
| 2,035,568 | 3/1936 | Pudliner | 248/222.1 |
| 3,017,657 | 1/1962 | Mills | 16/114 |
| 3,102,637 | 9/1963 | Scholl, Sr. | 211/69 |
| 3,152,818 | 10/1964 | Ivins | 287/20 |
| 3,501,182 | 3/1970 | Buchsbaum | 403/362 |
| 3,564,662 | 2/1971 | Dold | 211/70.6 X |
| 3,718,974 | 3/1973 | Buchtel et al. | 32/22 |
| 3,771,226 | 11/1973 | Lieb et al. | 32/22 |
| 3,918,161 | 11/1975 | Morgan et al. | 32/22 |
| 4,094,330 | 6/1978 | Jong | 403/362 X |
| 4,436,468 | 3/1984 | Ozaki et al. | 403/362 X |
| 4,880,122 | 11/1989 | Martindell | 211/70.6 |
| 4,883,316 | 11/1989 | Austin, Jr. et al. | 297/191 |
| 4,912,809 | 4/1990 | Scheuer | 16/114 |
| 4,952,146 | 8/1990 | Doty | 433/77 |
| 5,076,523 | 12/1991 | Wang | 248/222.1 |
| 5,088,671 | 2/1992 | Chen | 248/224.3 X |
| 5,176,423 | 1/1993 | Austin, Jr. et al. | |
| 5,286,130 | 2/1994 | Mueller | 403/165 X |

OTHER PUBLICATIONS

Takara Belmont 50-page Japanese language dental equipment catalog, cover and pp. 11–14, circa Jan. 1991.
A-Dec 117-page equipment catalog, cover and pp. 69, 73, 112, Jan. 1991.
KaVo "Estetica® 1042 Die Faszination des Fortschritts" German language 13-page brochure, cover and pp. 6–7, circa Jan. 1991.
Osada "FX Series" 31-page Japanese language brochure, cover and p. 6, circa Jan. 1991.
Siemens 27-page catalog, cover and pp. 6, 10, Feb. 1991.

*Primary Examiner*—Karen J. Chotkowski
*Attorney, Agent, or Firm*—Klarquist Sparkman Campbell Leigh & Whinston

[57] ABSTRACT

Apparatus useful for rotatably securing a dental instrument holder to a rod and enabling a convenient manual adjustment of the angular position of the instrument holder.

10 Claims, 2 Drawing Sheets

ROTATION ADJUSTMENT FOR DENTAL INSTRUMENT HOLDER

TECHNICAL FIELD

The dental field includes an array of holders for dental instruments and related items. The present invention is directed to a rotatably adjustable dental instrument holder.

BACKGROUND AND SUMMARY OF THE INVENTION

A dental instrument holder is a device that holds dental instruments within a dental operating theater, providing dental personnel with convenient access to those instruments. A dental instrument holder is usually mounted on an elongated rod, which may extend from a control unit or mechanical arm system. The elongated rod fits within a cylindrical cavity in the instrument holder and is usually secured within the cavity by a setscrew, which impinges upon the rod through a threaded setscrew hole in the holder.

The holder can be rotated slightly about the rod so that the user can select an orientation of the holder that provides the most convenient angle for holding the instruments. To provide for manual rotation adjustment for the instrument holder, a friction pad is provided between the setscrew and rod. The pad is pressed by the screw against the rod. The friction between the pad and rod provides a smooth resistance to instrument holder rotation. The amount of the resistance is adjustable by tightening or loosening the setscrew.

With the increased use of plastics in dental equipment holders, some disadvantages in the just-described system have become apparent. Notably, the high torques commonly applied to the setscrew when mounting the holder to the rod can cause compression cracks to form in the plastic adjacent to the threads of the setscrew.

The compression cracking occurs because the highly torqued setscrew causes significant permanent stresses in the plastic surrounding the setscrew. These stresses alone may be enough to cause compression fracture. Alternatively, the plastic may be permanently stressed so close to fracture that cracks can initiate from the minor impacts repeatedly sustained by the instrument holder as the instruments are removed and inserted.

In light of the disadvantages in the prior art, one objective of the present invention is to provide a rotation adjustment mechanism for a dental instrument holder, which mechanism does not cause compression fractures in the instrument holder.

A rotation adjustment for a dental instrument holder, in accordance with one aspect of the present invention, avoids the creation of harmful stresses in the plastic holder as a result of setscrew torquing. The subject invention includes a dental instrument holder with a cylindrical cavity that receives an end of an elongated rod. A setscrew hole is transversely located through the end of the rod. A setscrew is threaded in the hole. The end of the screw protrudes against the cavity wall to provide resistance to rotation of the instrument holder about the rod. The setscrew is accessed by a tool, such as an Allen wrench, through an access opening in the instrument holder. Because the setscrew is threaded within the rod, which is usually metallic, the above-described compression cracks in the holder are eliminated.

DETAILED DESCRIPTION OF THE PREFERRED EMBODIMENT

Figure 1:
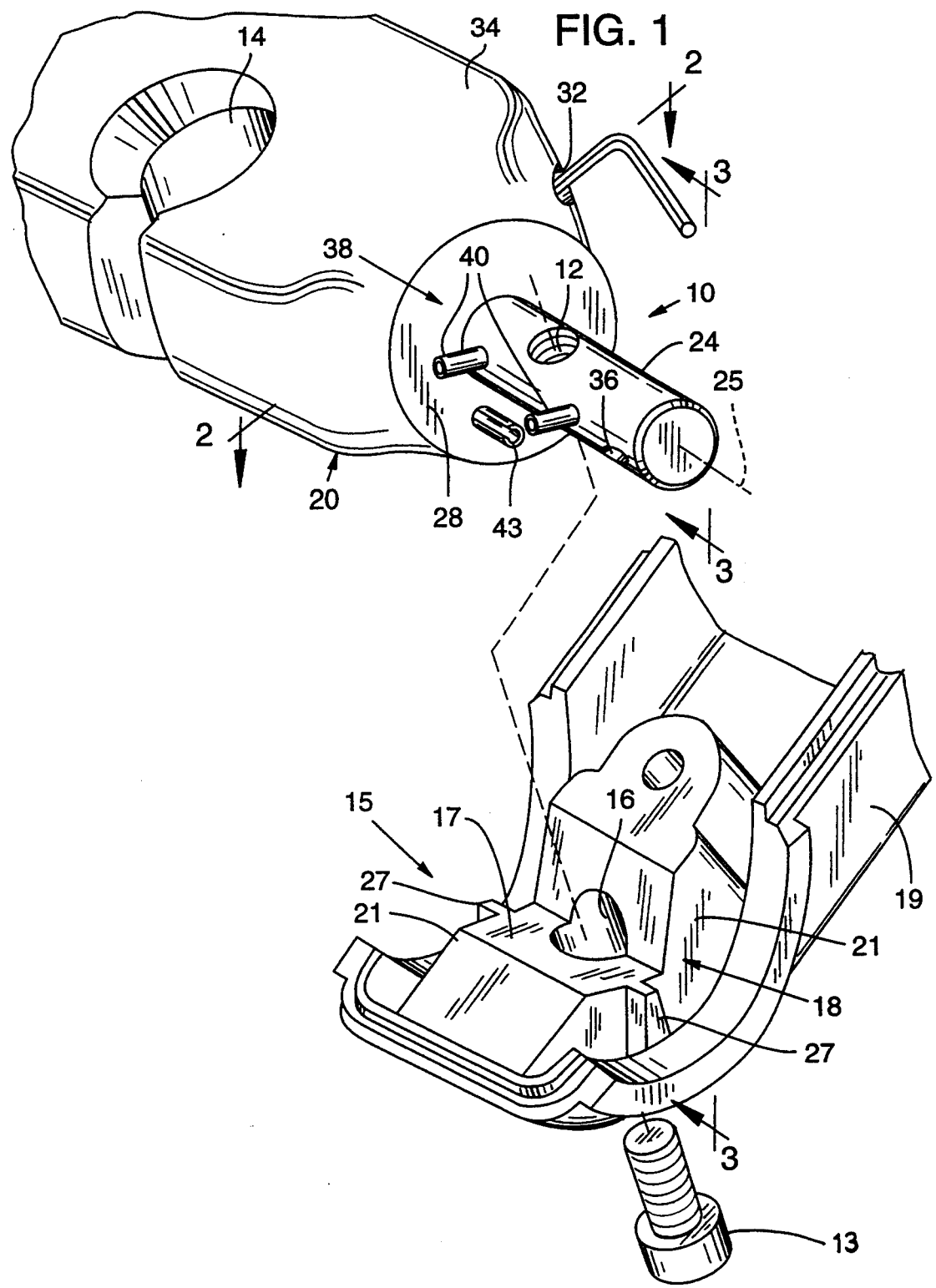
FIG. 1 is a fragmentary exploded perspective view of a dental instrument holder in accordance with a preferred embodiment of the present invention.

A dental instrument holder with a rotation adjustment 10 in accordance with a preferred embodiment of the present invention is illustrated in FIG. 1.

The dental instrument holder 20 of the illustrated embodiment is an elongated device with a series of openings or seats 14 (one seat shown in FIG. 1) for holding various dental instruments, such as drills. It is contemplated that instrument holders having any of a variety of shapes and seat sizes may employ the rotation adjustment of the present invention. While a single rotation adjustment mechanism for an instrument holder is described herein, it is to be understood that this invention also contemplates two such mechanisms, one on each end of a centrally-supported elongated rod 24. Hence, the two sets of holders and associated rotation adjustment mechanisms mirror each other about the center of the rod. In the drawings, the common components of each set are shown with the same reference numbers.

The center of the elongated rod 24 is mounted to a support 15 (FIG. 1), which may protrude from a control panel or similar structure. The support 15 includes a lower housing 19 in which is fastened a mounting block 18. An upper housing that joins the lower housing to cover the block 18 is not shown for illustrative purposes.

The block 18 includes an upwardly-facing, V-shaped clamping surface 17. The surface 17 extends between opposite sidewalls 21 of the mounting block 18. The sidewalls 21 are spaced from the sides of the lower housing 19, thereby to define a gap between the housing and walls, across which gap a rotation stop 27 protrudes from the sidewall 21 (one stop protruding from each sidewall 21). The function of the rotation stop 27 is described more fully below.

A clear aperture 16 is centrally disposed through the clamping surface 17 and extends completely through the block 18 and lower housing 19. A headed fastener 13 is placed through a countersunk end of the aperture 16 and is threaded into a threaded transverse hole 12 formed in the center of the rod 24. The rod is thus irrotatably secured to the support 15. Preferably, the hole 12 is tilted 30° counterclockwise (forward) from the vertical axis (see FIG. 3) when the rod 24 is mounted to the support 15.

Figure 2:
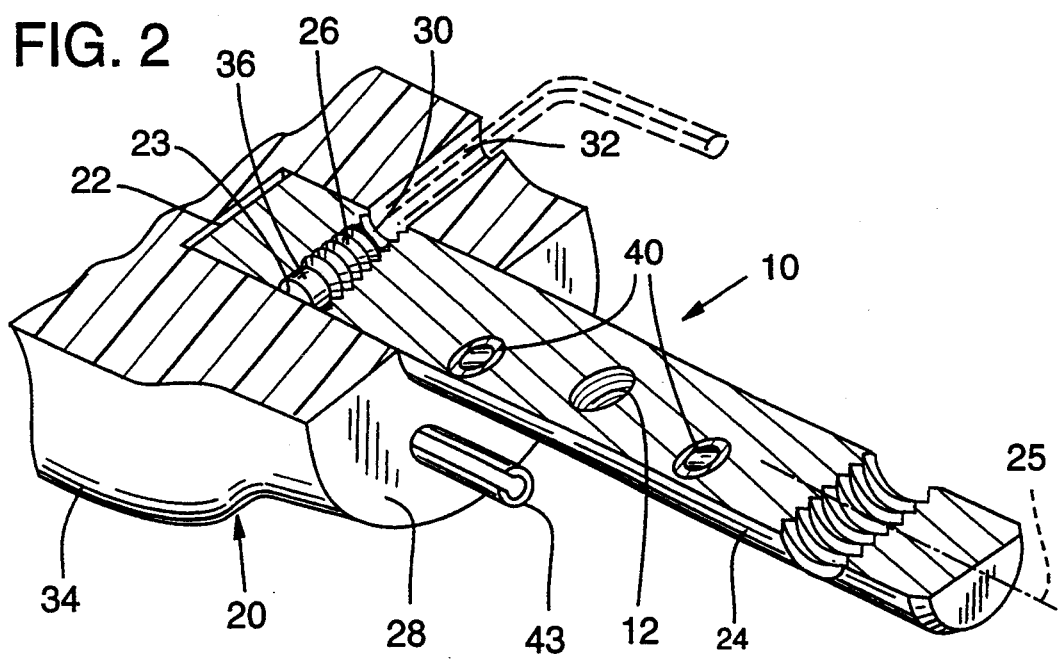
FIG. 2 is a section view of the dental instrument holder taken along line 2—2 of FIG. 1.

Each end of the rod 24 is provided with a setscrew hole 30 (FIG. 2). The axis of the setscrew hole 30 is arranged to be offset by an angle of 114°–116° clockwise from the axis of the central hole 12 in the rod.

The instrument holder 20 has a cylindrical cavity 22 formed in a flattened end 28 to receive an end of the rod 24. When the rod 24 is received within the cylindrical cavity 22, the setscrew hole 30 is completely within the cylindrical cavity 22.

A setscrew 26 is threaded into the setscrew hole 30. The setscrew hole 30, hence, the setscrew 26 is accessible through an access opening 32, which extends between the holder exterior surface 34 and the cylindrical wall 23 of the cavity 22. The access opening 32 is centered on the plane swept by the axis of the setscrew hole 30 as the holder 20 is rotated about the rod 24. In this way, the holder 20 can be rotated about the long axis 25 of the rod 24 until the access opening 32 aligns with the screw hole 30. An Allen wrench or similar tool may be inserted through the opening to rotate the screw 26.

A friction pad 36 is situated within the setscrew hole 30 between the setscrew 26 and the cavity wall 23. The pad is located at the end of the setscrew hole that is opposite the hole end that aligns with the access opening 32. The setscrew 26 is threaded into the setscrew hole and torqued to press the friction pad 36 against the cavity wall 23. The compression of the friction pad 36 against the cavity wall 23 provides the smooth frictional resistance to the rotation of the holder 20, without wear on the wall. The magnitude of the frictional resistance is adjustable by rotating the setscrew 26 to increase or decrease the compression of the friction pad 36.

In this embodiment, the friction pad 36 is composed of polyurethane, and the instrument holder member is composed of melamine phenolic plastic. The resulting coefficient of friction between the pad 36 and the cylinder wall 23 yields a preferred smooth frictional resistance. It is to be understood, however, that other pad and holder member materials will suffice. As an alternative, a separate bearing surface may be fitted within the cylindrical cavity wall to provide a smooth interface with the rod.

By providing the setscrew 26 within the elongated rod 24, the illustrated embodiment avoids the problems of the prior art. Specifically, the confinement of the setscrew 26 within the rod 24 isolates the plastic holder 20 from the stresses arising adjacent the setscrew 26 as the screw is torqued in the setscrew hole 30. The rod 24, which is typically stainless steel, has a strength to easily sustain any stresses generated about the setscrew hole 30. Moreover, the stresses generated in the plastic holder 20 by the pressure of the friction pad on the cavity wall 23 are low enough to avoid stress cracking in the plastic.

As mentioned above, the rotation adjustment includes mechanisms 38 for limiting the amount of rotation of the holder about the rod. These mechanisms prevent excessive rotation of the holder, which would cause the instruments to fall from the seats in the holder. The mechanism is configured to also prevent the alignment of the access opening 32 with the friction pad 36 in the setscrew hole 30 so that the pad can not inadvertently jam between the access hole and setscrew hole or pass out of the screw hole 30 through the access opening 32.

Figure 3:
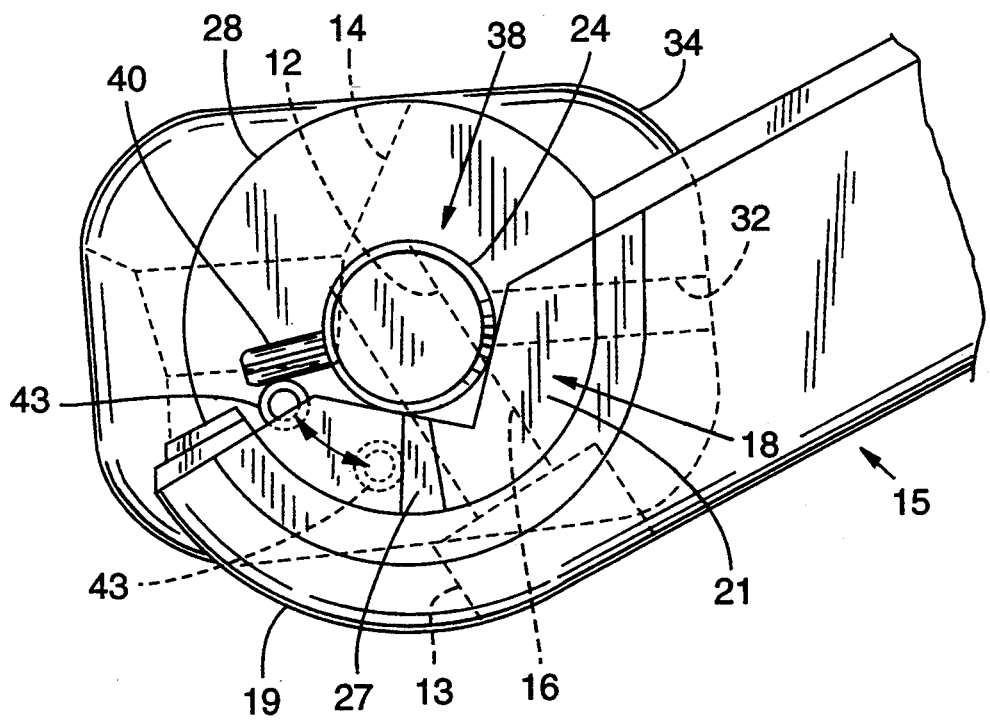
FIG. 3 is an elevational view of the assembly of FIG. 1 taken along line 3—3 of FIG. 1.

As best shown in FIGS. 1 and 3, a stationary limit pin 40 is press-fit within a hole in the rod 24 to extend from one side of the rod 24. The limit pin 40 is positioned within the gap between the flat end 28 of the instrument holder 20 and the adjacent sidewall 21 of the mounting block 18. As the rod 24 is viewed in a direction toward the flat end 28 of the holder (FIG. 3), the limit pin 40 extends laterally from the rod 24, at a position about 72° counterclockwise from the axis of the hole 12.

A stop pin 43 extends parallel to the rod 24, from a hole formed in the flat end 28 of the holder. The stop pin 43 comprises a roll pin and projects into the gap between the holder surface 28 and the mounting block sidewall 21. The stop pin 43 resides between the limit pin 40 and the rotation stop 27 that extends between the surface 28 and the sidewall 21.

As the holder 20 is rotated about the axis 25 of the rod 24, the stop pin 43 moves with the holder in a partial orbit around the rod 24. The orbit of the stop pin and, therefore, the rotation of the instrument holder 20, is limited in one direction as the stop pin 43 impinges upon the limit pin 40 (FIG. 3). In the opposite direction, the rotation of the holder is limited as the stop pin 43 encounters the rotation stop 27 that protrudes from the mounting block (as shown in the dashed lines depicting pin 43 in FIG. 3). The preferred configuration of the limit pin and rotation stop enables rotation of the holder 20 through a range of approximately 45° counterclockwise from a position of the holder where the instruments hang substantially vertically.

The stop pin 43, rotation stop 27, and limit pin 40 arrangement, limiting as it does the amount of rotation of the handle, thereby serves to prevent alignment of the access hole 32 with the end of the setscrew hole 30 that houses the friction pad 36. Consequently, the pad 36 is unable to align with and move out of the access hole 32.

Alternative rotation limiting mechanisms may function equally as well as those of the illustrated embodiment. For example, the stop pin 43 could be located between two limit pins attached to the rod 24 at a selected angular relationship. The stop pin 43, therefore, would move between those two limit pins to provide the range of holder 20 rotation corresponding to that angular relationship.

Another possibility is to replace the single stop pin of the illustrated embodiment with two stop pins, one stop pin on each side of a single limit pin.

This detailed description is set forth only for purpose of illustrating examples of the present invention and should not be considered to limit the scope of the invention in any way. Clearly, numerous additions, substitutions, and modifications can be made to these examples without departing from the scope of the invention which is defined by the appended claims and their equivalents.

The invention claimed is:

1. A mechanism for controlling rotation of a dental instrument holder, comprising:
   an elongated rod having a threaded hole extending laterally through an end of the rod;
   a fastener engaged in the threaded hole in the rod, the fastener having an end portion;
   a holder member having an opening for holding a dental instrument and having an internal wall defining a cavity for rotatably receiving the end of the rod, the cavity including an access opening formed in the holder member to permit the fastener to be threaded in the threaded hole while the rod end is within the cavity; and
   the end portion of the fastener slidably abutting the internal wall to provide a controlled frictional resistance as the holder member is rotated about the rod, apart from the end portion the fastener being spaced from the internal wall so that the holder member is rotatable through a range of angular motion with the sliding contact of the fastener end portion establishing a controlled resistance to the holder member rotation.

2. The mechanism according to claim 1,
   wherein the fastener end portion is an elastomeric pad situated adjacent one end of the fastener in the threaded hole, the pad being pressed by the fastener against the internal wall.

3. The mechanism according to claim 2, wherein the elastomeric pad is made of polyurethane.

4. The mechanism according to claim 1, wherein the rod is made of stainless steel, and the holder member is made of melamine phenolic plastic.

5. The mechanism according to claim 1, wherein the fastener is a setscrew.

6. The mechanism according to claim 1, wherein:
the holder member is rotatable through a range of angular motion about the rod, the range of motion being limited at a first end by a limit member fixedly extending from the rod and by a stop member extending from the holder member, the stop member moving with the rotatable holder member in a first direction to contact the limit member at the first end of the range of motion, thereby to limit rotation of the holder member.

7. A mechanism for controlling rotation of a dental instrument holder, comprising:
an elongated rod having a threaded hole extending laterally through an end of the rod;
a holder member having an opening for holding a dental instrument and having a cavity for rotatably receiving the end of the rod;
a fastener engaged in the threaded hole in the rod;
an access opening formed in the holder to intersect the cavity, thereby to permit the fastener to be threaded in the threaded hole while the rod end is within the cavity;
the holder member being rotatable through a range of angular motion about the rod, the range of motion being limited at a first end by a limit member fixedly extending from the rod and a stop member extending from the holder member, the stop member moving with the rotatable holder member in a first direction to contact the limit member at the first end of the range of motion, thereby to limit rotation of the holder member;
the holder member range of motion being limited at a second end by a second limit member fixedly extending from the rod, the stop member moving with the rotatable holder member in a second direction away from the first end of the range of motion to contact the second limit member at the second end of the range of motion.

8. A mechanism for controlling rotation of a dental instrument holder that is rotatably mounted to a rod, comprising:
a setscrew threaded laterally through the rod, the setscrew being configured for threading into contact with the holder that is mounted to the rod, the contact of the setscrew against the holder being exclusively slidable, the slidable contact permitting controlled rotation of the holder about the rod; and
access means formed in the holder to permit threading of the fastener while the holder is mounted to the rod end.

9. The mechanism of claim 8, further comprising an elastomeric pad situated between the fastener and the holder to provide frictional resistance to rotation of the holder.

10. The mechanism of claim 9, further comprising limiting means for limiting the amount of rotation of the holder about the rod.

* * * * *